(12) United States Patent
Nauche

(10) Patent No.: US 7,976,160 B2
(45) Date of Patent: Jul. 12, 2011

(54) AUTOMATIC PUPILLOMETER WITH VISUAL VERIFICATION

(75) Inventor: Michel Nauche, Charenton-le-Pont (FR)

(73) Assignee: Essilor International, Charenton-Le-Pont (FR)

( * ) Notice: Subject to any disclaimer, the term of this patent is extended or adjusted under 35 U.S.C. 154(b) by 0 days.

(21) Appl. No.: 12/680,940

(22) PCT Filed: Oct. 1, 2008

(86) PCT No.: PCT/FR2008/051766
§ 371 (c)(1),
(2), (4) Date: Mar. 31, 2010

(87) PCT Pub. No.: WO2009/053570
PCT Pub. Date: Apr. 30, 2009

(65) Prior Publication Data
US 2010/0220286 A1     Sep. 2, 2010

(30) Foreign Application Priority Data
Oct. 9, 2007   (FR) ...................................... 07 58167

(51) Int. Cl.
*A61B 3/10* (2006.01)

(52) U.S. Cl. ........................................ 351/204; 351/221
(58) Field of Classification Search .................. 351/200, 351/204, 205, 208, 210, 221, 246; 600/558
See application file for complete search history.

(56) References Cited

U.S. PATENT DOCUMENTS

| | | | | |
|---|---|---|---|---|
| 5,661,538 A | * | 8/1997 | Carter | 351/237 |
| 7,384,144 B2 | * | 6/2008 | Ross-Messemer et al. | 351/204 |
| 7,740,355 B2 | * | 6/2010 | Sessner et al. | 351/204 |

* cited by examiner

*Primary Examiner* — Jack Dinh
(74) *Attorney, Agent, or Firm* — Sofer & Haroun, LLP

(57) ABSTRACT

The invention relates to an automatic pupillometer comprising a light source suitable for generating a corneal reflection on at least one of the eyes of an individual facing first and second windows, a collimator lens serving at least to position the light source to correspond to far vision of the individual, a detection receiver for automatically locating said reflection, and a calculator for calculating the pupillary distance of said individual. According to the invention, the pupillometer also comprises a third window where the eye of an observer responsible for the measurement is designed to be placed in the vicinity of the focus of said lens so as to view and verify measurement conditions.

11 Claims, 3 Drawing Sheets

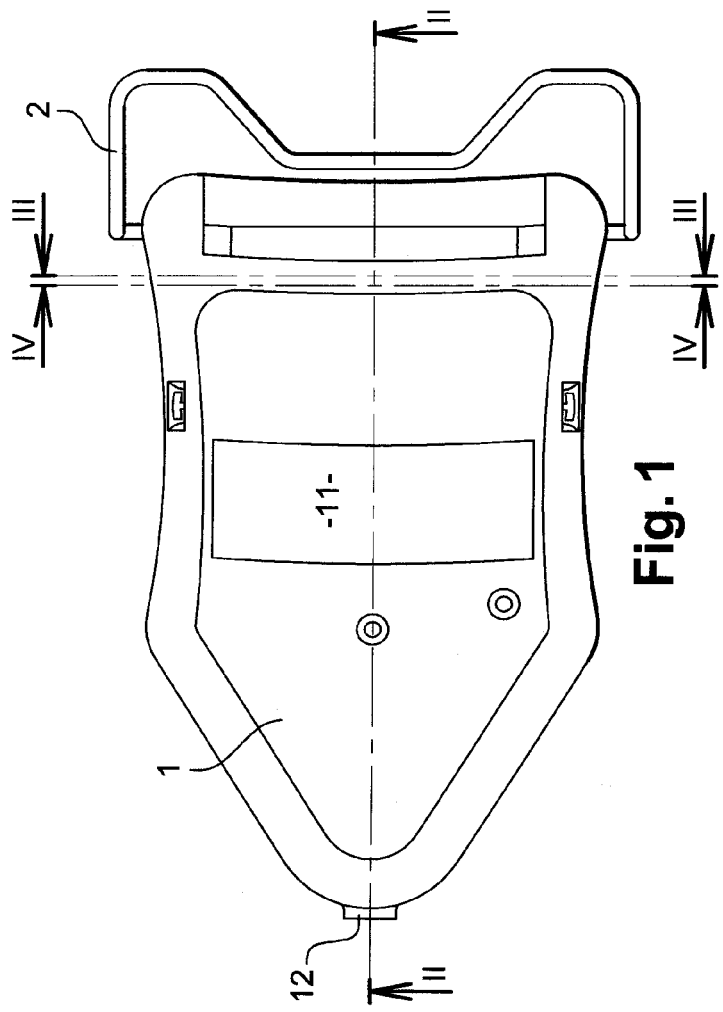
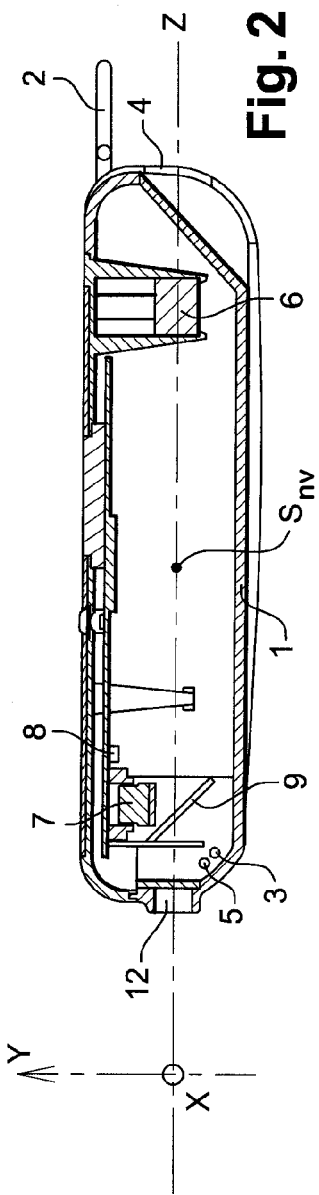
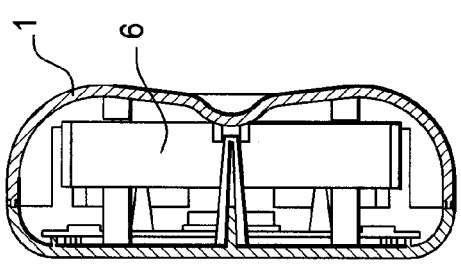
Fig. 1
Fig. 2
Fig. 3
Fig. 4

AUTOMATIC PUPILLOMETER WITH VISUAL VERIFICATION

Related Applications:

This application is a National Phase Application of PCT/FR2008/051766, filed on Oct. 1, 2008, which in turn claims the benefit of priority from French Patent Application No. 07 58167, filed on Oct. 9, 2007, the entirety of which are incorporated herein by reference.

BACKGROUND OF THE INVENTION

1. Field of the Invention

The invention relates to an automatic pupillometer with visual verification.

A pupillometer is an appliance designed to measure the pupillary distance of an individual. It consists in using a light source suitable for generating a corneal reflection on at least one of the eyes of the individual, and in proceeding to locate said reflection.

2. Description of the Related Art

Such a pupillometer may be manual, e.g. as described in patent document FR 1 506 352.

The appliance is then provided with three windows, two windows reproducing the eyeglass frame that is to be placed on the nose of the individual, and an opposite window where the eye of an observer responsible for the measurement is placed at the focus of a collimator lens enabling the light source to be positioned at infinity to correspond to the far vision of the individual. The lens may be movable in translation along the sighting axis, so as to enable a near vision measurement to be taken; the lens is then moved closer to the light source. The observer in the measurement position moves a movable marker and causes it to correspond with the corneal reflection so as to obtain the trace of the axis of each pupil and thus measure the pupillary half-distance for each eye of the individual.

That type of manual pupillometer takes time and raises problems with measurement accuracy.

More recently, automatic pupillometers have been proposed, e.g. as described in patent document FR 2 618 666.

The light rays corresponding to the corneal reflections therein are directed towards a detection receiver, which is a photosensitive receiver or a photodiode, and the pupillary distance is then calculated electronically. There is no need for an observer, with the measurement being performed completely automatically.

That type of pupillometer, which is particularly accurate since it is independent of an operator, nevertheless raises the following problems.

The individual whose pupillary distance is to be measured may behave in a way that impedes good measurement. For example, the individual may close the eyes, may blink, or may look in the wrong direction, i.e. away from the light source. This can lead to a wrong measurement of the pupillary half-distance, or indeed to a wrong measurement of the pupillary distance, if the individual is not looking at infinity. In addition, ambient lighting conditions may disturb the measurement, thereby giving rise to inaccurate values.

In an automatic pupillometer, it is presently not possible to detect such an error.

Logically, and given the way this technique of measurement by pupillometry is developing, it is possible to envisage verifying proper positioning of the eyes of an individual in a manner that is likewise automatic.

Nevertheless, it is not always easy to verify that the eyes are open, since it can happen for example that a corneal reflection is partially visible, with the photograph being taken at an instant when the eyelid is moving, thus leading to a result being obtained that is approximate in terms of accuracy, but that cannot be said to be wrong.

When verification is possible, it is necessary to envisage using electronic components that are capable of performing numerous calculations in order to analyze the image. Such components are generally quite expensive, bulky, and they consume large amounts of electrical energy, thus raising difficulties for an appliance that is portable.

OBJECTS AND SUMMARY

The invention solves this problem of verifying the proper positioning of an individual's eyes in an automatic pupillometer.

To do this, the invention provides an automatic pupillometer comprising a light source suitable for generating a corneal reflection on at least one of the eyes of an individual facing first and second windows, a collimator lens serving at least to position the light source to correspond to far vision of the individual, a detection receiver for automatically locating said reflection, and a calculator for calculating the pupillary distance of said individual, wherein the pupillometer also comprises a third window where the eye of an observer responsible for the measurement is designed to be placed in the vicinity of the focus of said lens so as to view and verify measurement conditions.

In a preferred embodiment, after verification, the observer validates the measurement, and in order to make this possible, the pupillometer includes actuator means designed to be actuated by said observer and to validate said measurement.

Advantageously, said detection receiver is a camera.

It may include at least one mirror serving to transfer said corneal reflection towards said detection receiver.

Advantageously, the pupillometer in accordance with the invention includes a monocular occultation arrangement.

Said occultation arrangement may comprise two screens having electrically-controlled diaphragms that are disposed respectively facing the first and second windows.

Preferably, said calculator includes a module for calculating the pupillary distance of said individual in near vision.

Said calculator may include a module for calculating the radius of the eye of said individual.

Said calculator may include a module for correcting said measurement as a function of the distances of the eyes of said individual from the corresponding eyeglass lenses.

Advantageously, said light source is an infrared source.

The pupillometer may also include a light source for near vision measurement.

BRIEF DESCRIPTION OF THE DRAWINGS

The invention is described in greater detail below with reference to figures that merely show preferred embodiments of the invention.

FIG. 1 is a plan view of a pupillometer in accordance with the invention.

FIG. 2 is a section view on II-II of FIG. 1.

FIG. 3 is a section view on of FIG. 1.

FIG. 4 is a section view on IV-IV of FIG. 1.

DETAILED DESCRIPTION

Figure 5:
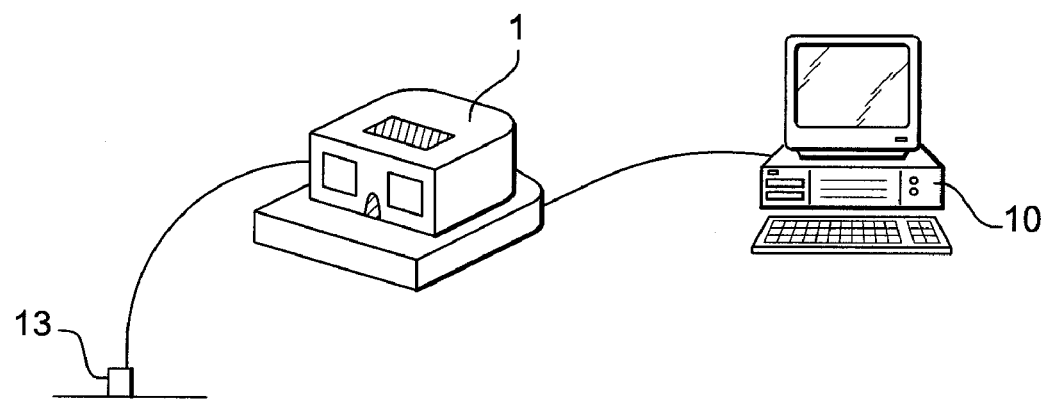
FIG. 5 is a view showing the pupillometer as a whole.

An automatic pupillometer in accordance with the invention is shown in detail in FIGS. 1 to 4.

The pupillometer comprises a housing 1 provided with a portion 2 reproducing an eyeglass frame for placing on the nose of an individual whose pupillary distance is to be measured.

Inside the housing, the automatic pupillometer comprises:
- an infrared light source 3 suitable for generating a corneal reflection on at least one of the eyes of the individual, each of which eyes faces a respective first or second window 4;
- a visible light source 5 placed beside the infrared light source and serving to be looked at and sighted by the individual;
- a collimator lens 6 serving at least to position the light source 3, 5 so as to correspond to far vision of the individual, the infrared light source 3 and the visible light source 5 being located in the vicinity of the focus of the lens 6;
- a detection receiver, constituted by a camera 7 for automatically locating said reflection; and
- a calculator carried by an electronics card 8 contained in the housing 1 and carrying the camera, the calculator serving to calculate the pupillary distance of the individual.

Given the positioning of the camera 7, a transparent mirror 9 inclined at 45° serves to transfer the light flux corresponding to the corneal reflection towards the camera 7.

The electronics card 3 also includes a light-emitting diode (LED) screen or a liquid crystal display (LCD) type display 11 disposed in front of an opening arranged in the housing and serving to display the measured capillary distance and capillary half-distances.

Facing the two windows 4 through which the individual looks and sights, the housing includes a third window 12 where the eye of an observer responsible for taking the measurements is to be placed at the focus of the collimator lens 6, in order to verify measurement conditions.

The pupillometer also has a monocular occultation arrangement constituted by two screens 13, 14 with electrically-controlled diaphragms disposed respectively facing the first and second windows 4.

The method of taking the measurement and the operation of such a pupillometer are as follows.

The observer responsible for the measurement places the housing 1 of the pupillometer on the person's face, and then by looking in through the third window 12 verifies visually whether the person is indeed looking in the right direction, i.e. towards the visible light source 5, by observing whether the corneal reflections are properly centered relative to the pupils of the eyes, and that the person is in a stable gaze position, i.e. both eyes are indeed open. When these conditions are satisfied, the observer launches measurement by pressing on button type actuator means 13, or else confirms the most recently performed measurement, likewise by pressing on said button 13, which is electronically connected to the calculator.

Functionally, the person gazing towards the visible light source 5 through the two windows 4 gives rise to an almost identical gaze towards the infrared light source 3. This infrared light source 3 generates a corneal reflection on each of the eyes of the individual. Part of the corneal reflection is transmitted towards the camera 7 by reflection on the semitransparent mirror 9.

The observer observes the corneal reflections generated by the visible light source 5.

An infrared source 3 is used as well as the visible source 5 in order to obtain a better image on the camera, since the intensity of the reflection on the cornea can be high without dazzling the person being observed, and since the impact of parasitic ambient light flux is reduced. Nevertheless, it is possible to use the visible light source only by briefly increasing the intensity of the light with a flash of light, at the moment the measurement is confirmed.

When using an infrared source, it is preferable to use an infrared filter, the filter being adapted to pass only wavelengths that correspond to the infrared emission from the source. The filter is placed either in front of the sensor of the camera, or in front of the camera, or else it is alternatively implemented by means of the mirror 9, with the mirror 9 then reflecting only the infrared emission while allowing other wavelengths to pass therethrough. This type of mirror is referred to as a "cold mirror".

The location data from the camera is transmitted to the calculator, which may be an unsophisticated device, e.g. of the ADSP-BF531 type from the supplier Analog Devices. Measurement is performed by calculating the center of gravity of points presenting intensity that is above some threshold in two zones that correspond respectively to the right eye and to the left eye. This calculation requires very little power and may be performed simultaneously with the camera taking the image.

The pupillometer may be placed on a stand, which may automatically trigger the sending of measurements to processing software of a computer 10, and which may also serve to recharge batteries, as shown in FIG. 5. The connection between the pupillometer and the computer may also be provided via a wireless network, of WiFi or equivalent type.

The measurement may be associated with or replaced by a monocular measurement of half-distances by using the two screens 13 and 14 having electrically-controlled diaphragms. By adjusting the voltages applied thereto, such screens can be caused to switch from a transparent state to a state of occultation, and back again, independently of each other. One of the screens may therefore be set to the occultation state so that a view is provided only of the person's other eye.

This makes it possible to detect problems of strabismus, with the eye that is not focusing on the light source being caused to move when the other eye is occulted. It is thus possible to detect problems of amblyopia, i.e. circumstances in which one eye sees nothing, since when the normal eye is occulted, the amblyopic eye gives a half-distance that is different from the half-distance obtained by a binocular measurement.

The calculator also has a module for calculating the pupillary distance of the individual in near vision.

The near vision measurement can be deduced from the far vision measurement. To do this, it suffices to know the radius R of the eye, which is estimated as being equal to the average radius. The following formula is then used:

$$R = D(PDd\_fv - PDd\_nv)/PDd\_fv$$

giving:

$$PDd\_nv = PDd\_fv - R_{av} \times PDd\_fv/D$$

where:

PDd_fv is the pupillary half-distance in far vision;

PDd_nv is the pupillary half-distance in near vision; and

D is the distance between the light source 3 and the individual's eye in near vision.

The calculator may also include a module for correcting the measured pupillary distance as a function of the distance between the individual's eyes and the corresponding eyeglass lenses.

Figure 6:
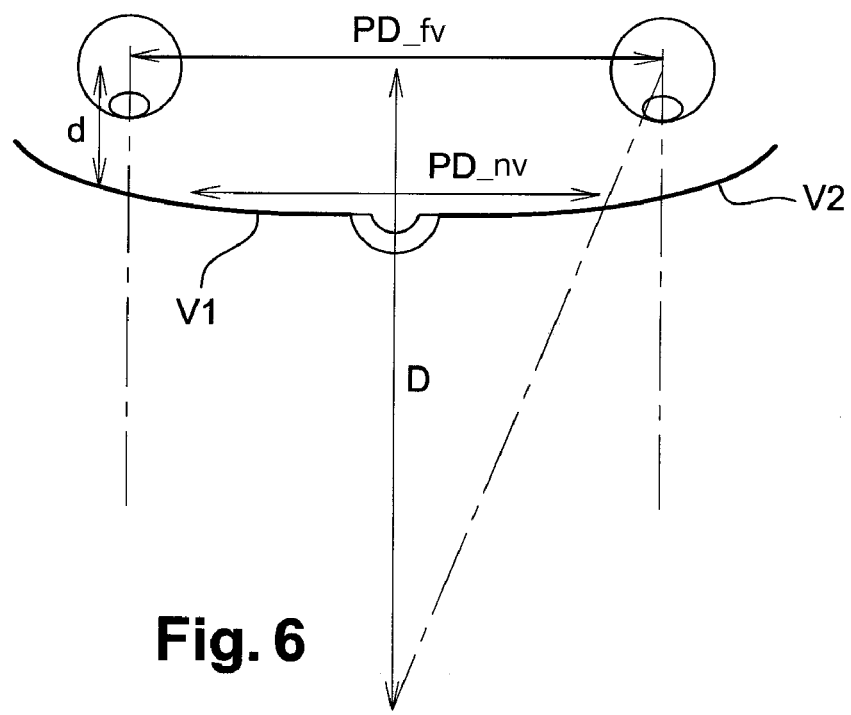
FIG. 6 is a diagram illustrating the measurement correction as a function of the distance between the eyes of an individual and the lenses of that individual's eyeglasses.

With reference to FIG. 6, the value of the pupillary distance in near vision offset to the plane of the frame is directly impacted by the distance d between each eyeglass lens $V_1$, $V_2$ and the center of rotation of the corresponding eye, and this distance is not taken into account in present-day pupillometers. In the pupillometer in accordance with the invention, the value for this distance d is input and a value for the near vision pupillary distance is calculated as follows:

$$PD\_nv = PD\_fv \times (D-d)/D$$

with:

PD_fv pupillary distance in far vision:

PD_nv pupillary distance in near vision in the plane of the frame; and

D is the real or theoretical presentation distance in near vision.

Thus, while taking measurements for far vision only, it is possible to determine accurately the pupillary distance in near vision for different values of D, providing the distance d between the lens and the center of the eye is input.

Variants may be applied to such a pupillometer while remaining within the ambit of the invention.

Depending on the embodiment described, the paths of the light ray going from the light source 3 towards the eye of the person, and of the light ray going from the corneal reflection towards the camera 7 are slightly offset because of the offsets along the observation, axis Z and the vertical axis Y of the infrared light source 3 relative to the camera. The offset in the Z direction generates small inaccuracies in the measured pupillary half-distances that can be corrected, e.g. by using a correction table that gives the correction to be applied to each of the right and left pupillary half-distances as a function of their values.

Figure 7:
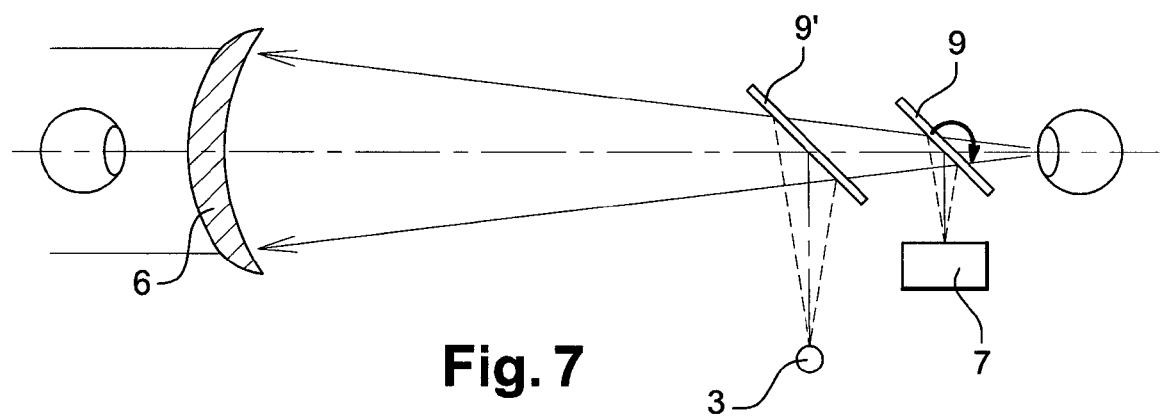
FIGS. 7 and 8 are views of functional configurations of variants of the invention.

The paths may be made to coincide to a large extent by using a plurality of semitransparent mirrors, one mirror 9' being specific to the light source and the other mirror 9 being specific to the camera, as shown in FIG. 7.

Instead of using a semitransparent mirror, it is possible to use a removable rotary mirror 9 specific to the camera, as represented by an arrow. The mirror is then retracted synchronously with the press on the button 13 so as to enable the camera to receive the light flux, and it then returns automatically to its initial position. This synchronization may be controlled electrically or mechanically. This solution serves to obtain light flux that is greater than when using a stationary semitransparent mirror.

It is also possible to use a "cold" mirror that reflects infrared light only. The infrared light source 3 is then necessarily located downstream from the mirror. This configuration makes it possible to obtain a maximum level of light flux in the visible for the observer and in the infrared for the camera, since the visible light flux is transmitted in full by the mirror 9, whereas the infrared light flux is reflected in full towards the camera. Such a cold mirror thus also performs a wavelength filtering function, since only wavelengths corresponding to the infrared light source 3, 6 are transmitted to the camera.

Figure 8:
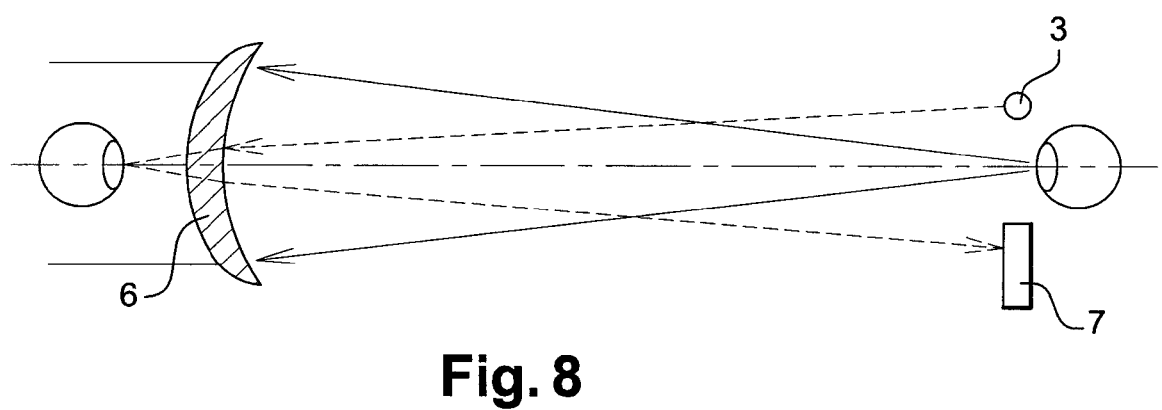

As shown in FIG. 8, it is also possible to offset the path of the light ray going from the light source 3 towards the person's eye and of the light ray going from the corneal reflection towards the camera 7 so that there is no need for any semitransparent mirror. Nevertheless, the observer responsible for the measurement then observes the corneal reflection offset relative to the person's pupil.

When the offset is vertical, as shown in FIG. 8, no measurement correction is needed.

When the offset is horizontal, it is possible to make provision for an average correction of the measured half-distances, by adding or subtracting a predetermined constant value from the measurements that are obtained.

The users concerned by a pupillometer in accordance with the invention are opticians, i.e. the observers responsible for taking the measurement. The appliance enables them to measure pupillary half-distances quickly and accurately, and the appliance is also of a cost similar to that of present appliances.

The collimator lens 6 may be mounted so as to be movable in translation, thereby making it possible to measure directly the pupillary distance in near vision, or it is possible to add a light source that is adapted to perform the test in near vision and that is situated between the lens and its focal point, as specified in FIG. 2 by the point $S_{nv}$.

Under such circumstances, the calculator may include a module for calculating the radius of the eye and the appliance may more advantageously be used for preparing lenses for eyeglass frames.

It is possible to measure the radius of the eye from measurements of the half-spacing in near vision and in far vision. The following relationship applies:

$$R = D \times (PDd\_fv - PDd\_nv)/PDd\_fv$$

The invention claimed is:

1. An automatic pupillometer comprising;
   a light source suitable for generating a corneal reflection on at least one of the eyes of an individual facing first and second windows,
   a collimator lens serving at least to position the light source to correspond to far vision of the individual,
   a detection receiver for automatically locating said reflection, and
   a calculator for calculating the pupillary distance of said individual, wherein the pupillometer has a third window where the eye of an observer responsible for the measurement is designed to be placed in the vicinity of the focus of said lens so as to view and verify measurement conditions.

2. A pupillometer according to claim 1, wherein said pupillometer includes actuator means designed to be actuated by said observer and to confirm said measurement.

3. A pupillometer according to claim 1, wherein said detection receiver is a camera.

4. A pupillometer according to claim 1, wherein said pupillometer includes at least one mirror serving to transfer said corneal reflection towards said detection receiver.

5. A pupillometer according to claim 1, wherein said pupillometer includes a monocular occultation arrangement.

6. A pupillometer according to claim 1, wherein said occultation arrangement comprises two screens having electrically-controlled diaphragms that are disposed respectively facing the first and second windows.

7. A pupillometer according to claim 1, wherein said calculator includes a module for calculating the pupillary distance of said individual in near vision.

8. A pupillometer according to claim 1, wherein said calculator includes a module for calculating the radius of the eye of said individual.

9. A pupillometer according to claim 1, wherein said calculator includes a module for correcting said measurement as a function of the distances of the eyes of said individual from the corresponding eyeglass lenses.

10. A pupillometer according to claim 1, wherein said light source is an infrared source.

11. A pupillometer according to claim 1, wherein said pupillometer also includes a light source for near vision measurement.

* * * * *